(12) United States Patent
Toyama (10) Patent No.: US 7,850,678 B2
(45) Date of Patent: Dec. 14, 2010

(54) ENDOSCOPE, ENDOSCOPE SYSTEM, AND METHOD OF MANUFACTURING ENDOSCOPE (75) Inventor: Ryuichi Toyama, Hachioji (JP)

(73) Assignee: Olympus Medical Systems Corp., Tokyo (JP)

(*) Notice: Subject to any disclaimer, the term of this patent is extended or adjusted under 35 U.S.C. 154(b) by 1014 days.

(21) Appl. No.: 11/650,526

(22) Filed: Jan. 5, 2007

(65) Prior Publication Data
US 2007/0167674 A1 Jul. 19, 2007

(30) Foreign Application Priority Data
Jan. 13, 2006 (JP) ............... 2006-006783

(51) Int. Cl.
A61B 1/00 (2006.01)
(52) U.S. Cl. ............... 606/1; 600/139; 600/140; 600/101
(58) Field of Classification Search ............ 606/1; 604/165.04; 600/114, 139, 140
See application file for complete search history.

(56) References Cited
U.S. PATENT DOCUMENTS
6,425,418 B1 * 7/2002 Maeda et al. ............... 138/133
6,503,193 B1 * 1/2003 Iwasaki et al. .............. 600/140
7,048,717 B1 * 5/2006 Frassica ................. 604/165.04
2003/0220543 A1 * 11/2003 Abe .......................... 600/140
2004/0087885 A1 * 5/2004 Kawano et al. ................ 604/8
2005/0272976 A1 * 12/2005 Tanaka et al. ............... 600/114

FOREIGN PATENT DOCUMENTS
JP 10-113396 5/1998
JP 2004-081656 3/2004

* cited by examiner

Primary Examiner—Henry M Johnson, III
Assistant Examiner—Jeffrey B Lipitz
(74) Attorney, Agent, or Firm—Scully, Scott, Murphy & Presser, P.C.

(57) ABSTRACT

An endoscope of the invention is the endoscope for applying a propulsion force in a direction of insertion axis of an insertion portion main body in accordance with rotation of the insertion portion main body based on driving force of a driving member, and the endoscope includes a flexible elongated inner layer tube configured as a shaft of the insertion portion; and a spiral-shaped portion rotatable around the inner layer tube as an axial center based on the driving force of a motor, the spiral-shaped portion forming an outer surface of the insertion portion main body, in which the spiral-shaped portion is formed by a nondensely wound coil and a resin thin film provided so as to cover gaps of a wire forming the metal coil.

12 Claims, 9 Drawing Sheets

ENDOSCOPE, ENDOSCOPE SYSTEM, AND METHOD OF MANUFACTURING ENDOSCOPE

This application claims benefit of Japanese Application No. 2006-006783 filed in Japan on Jan. 13, 2006, the contents of which are incorporated by this reference.

BACKGROUND OF THE INVENTION

1. Field of the Invention

The present invention relates to an endoscope which applies a propulsion force in a direction of insertion axis of an insertion portion thereof corresponding to rotation of the insertion portion based on a driving force of a driving member, an endoscope system, and a method of manufacturing the endoscope.

2. Description of Related Art

Conventionally, an endoscope for medical use has been widely used. The endoscope, for example, can provide observation of an affected part and the like within a body cavity by inserting an elongated insertion portion into the body cavity and various treatments using a treatment instrument inserted into a forceps channel as needed. The endoscope includes on a distal end side of the insertion portion thereof a freely bendable bending portion. In the endoscope, the bending portion is bent and operated in up/down and left/right directions by operation of a bending operation knob.

When the endoscope device is inserted into a convoluted intracavital canal, for example, a lumen forming a loop of 360 degrees such as the large intestine, the bending portion is bent and operated by the operation of the bending operation knob, while the insertion portion is operated and twisted to be inserted toward an observation target position.

However, such an operation of the endoscope requires mastery to be able to insert the insertion portion smoothly in a short period of time into a deep part in the convoluted large intestine. Therefore, it is concerned that an inexperienced operator, in inserting the insertion portion into the deep part in the large intestine, loses the insertion direction and has trouble in the insertion, and greatly changes the way the intestine runs.

Therefore, various proposals have conventionally been made for improving the insertability of the insertion portion. For example, Japanese unexamined patent publication No. 10-113396 discloses a propulsion device for medical apparatus capable of easily and low-invasively guiding a medical apparatus into a deep part of an intracavital canal.

The propulsion device has a rotation member provided in the axial direction thereof with a diagonal rib serving as a propulsion force generating portion. Accordingly, in the propulsion device described in the above-described publication, with rotational motion of the rotation member, rotational force of the rotation member is converted into a propulsion force by the rib, and the medical apparatus linked to the propulsion device is moved toward the direction of the deep part of the intracavital canal by the propulsion force. According to this, the propulsion device described in Japanese unexamined patent publication No. 10-113396 is capable of inserting the medical apparatus into a body cavity without putting a physical burden on a patient.

SUMMARY OF THE INVENTION

In short, an endoscope of the present invention is one for applying a propulsion force in a direction of insertion axis of an insertion portion in accordance with rotation of the insertion portion based on a driving force of a driving member, and the endoscope comprises: a flexible elongated tube configured as a shaft of the insertion portion; and a spiral-shaped portion rotatable around the tube as an axial center based on the driving force of the driving member, the spiral-shaped portion forming an outer surface of the insertion portion; in which the spiral-shaped portion includes a nondensely wound coil and a resin thin film continuously provided so as to cover gaps of a wire forming the metal coil.

The above and other objects, features and advantages of the invention will become more clearly understood from the following description referring to the accompanying drawings.

DETAILED DESCRIPTION OF PREFERRED EMBODIMENTS

Below, description will be made on the present embodiment with reference to the drawings.

Figure 1:
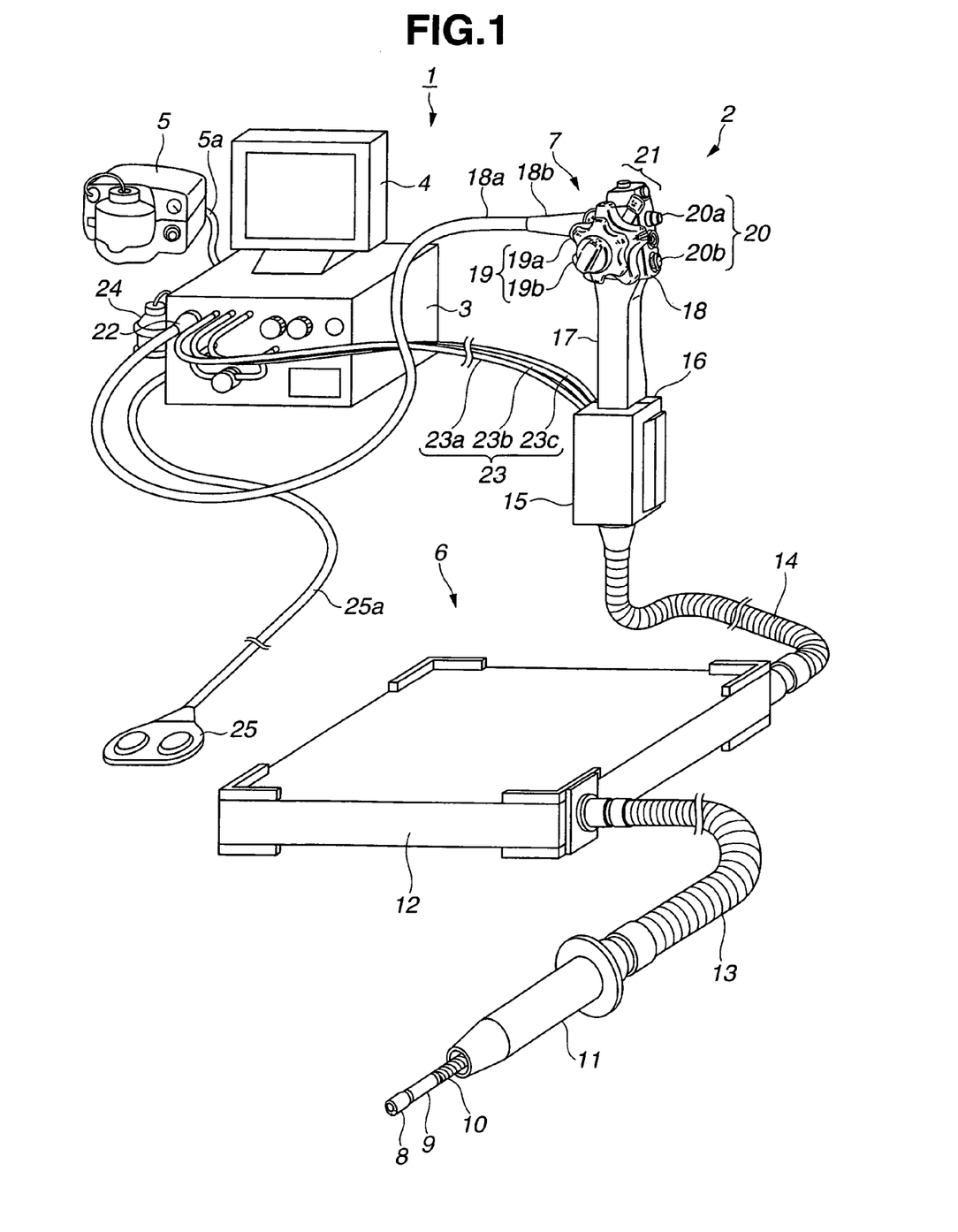
FIG. 1 is an appearance view showing a whole configuration of a rotating self-propelled endoscope system provided with an endoscope of the present embodiment.
Figure 2:
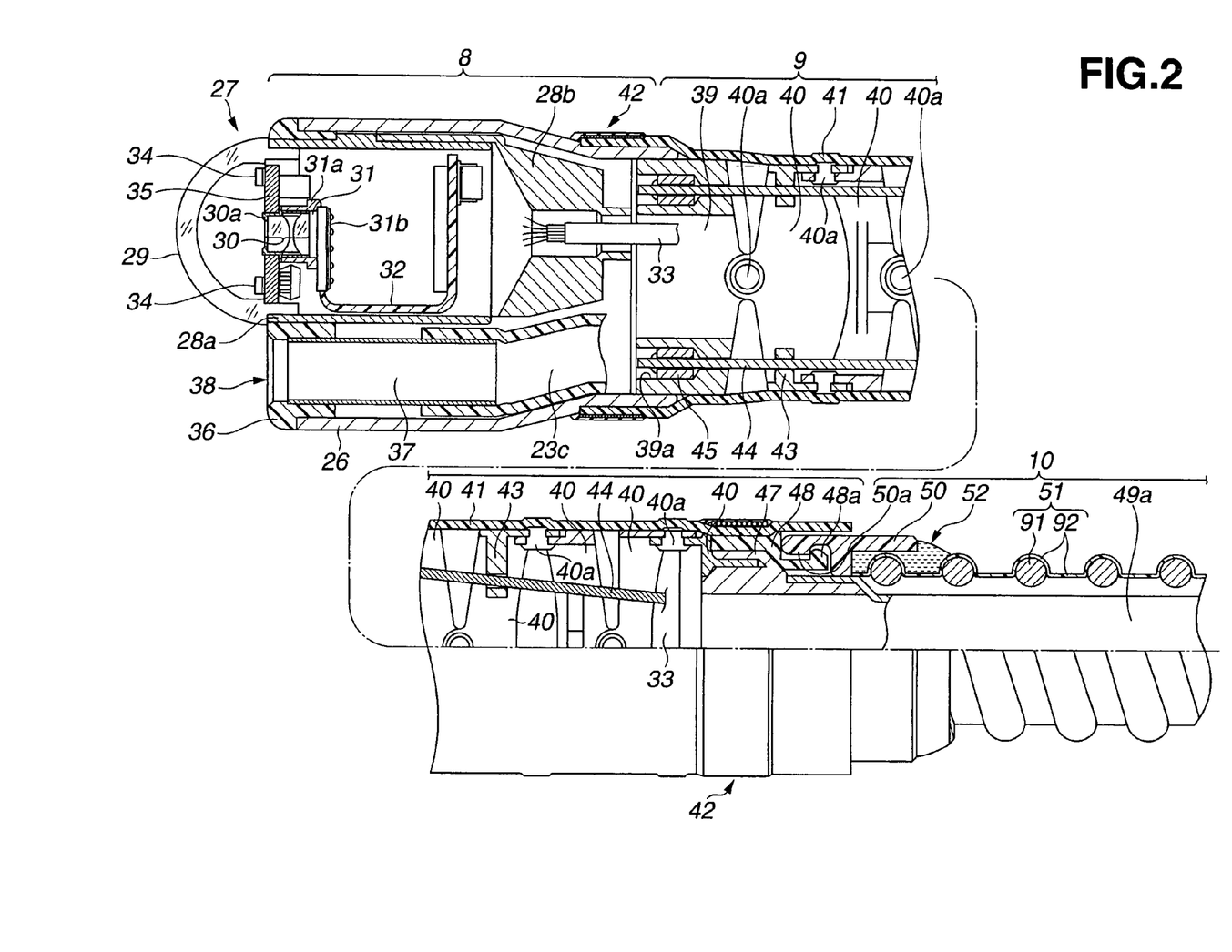
FIG. 2 is a cross-sectional view showing a distal end portion, a bending portion, and a part of a spiral-shaped portion of the endoscope of FIG. 1.

FIGS. 1 to 10 relate to the present embodiment, in which FIG. 1 is an appearance view showing a whole configuration of a rotating self-propelled endoscope system provided with an endoscope of the present embodiment and FIG. 2 is a cross-sectional view showing a distal end portion, bending portion, and a part of a spiral-shaped portion of the endoscope of FIG. 1.

Figure 3:
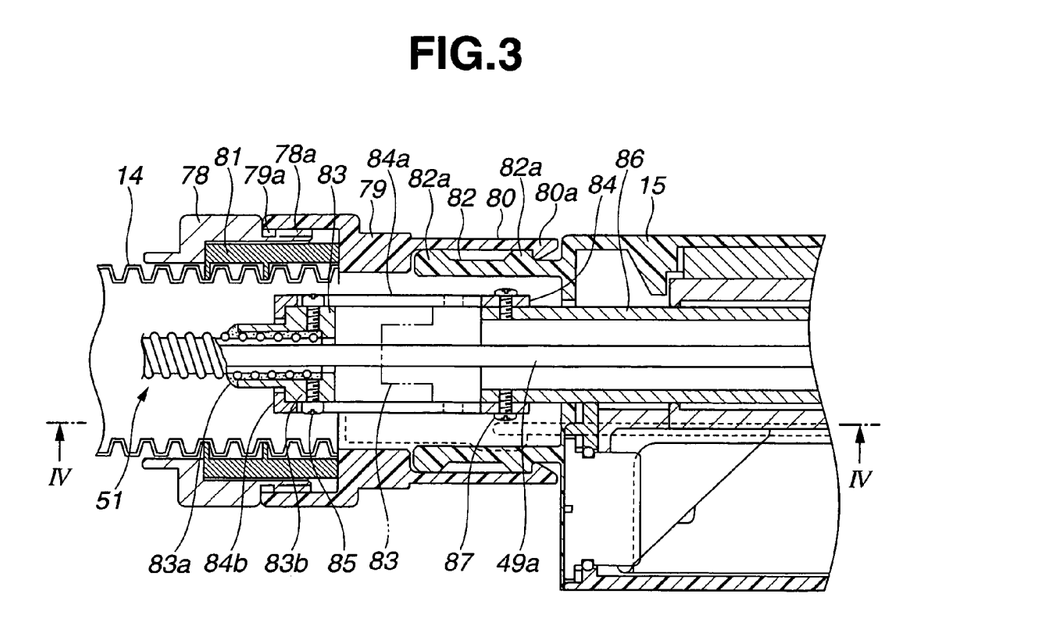
FIG. 3 is a cross-sectional view showing a part of a connector cover to which an operation portion-side guide tube of FIG. 1 is connected.
Figure 4:
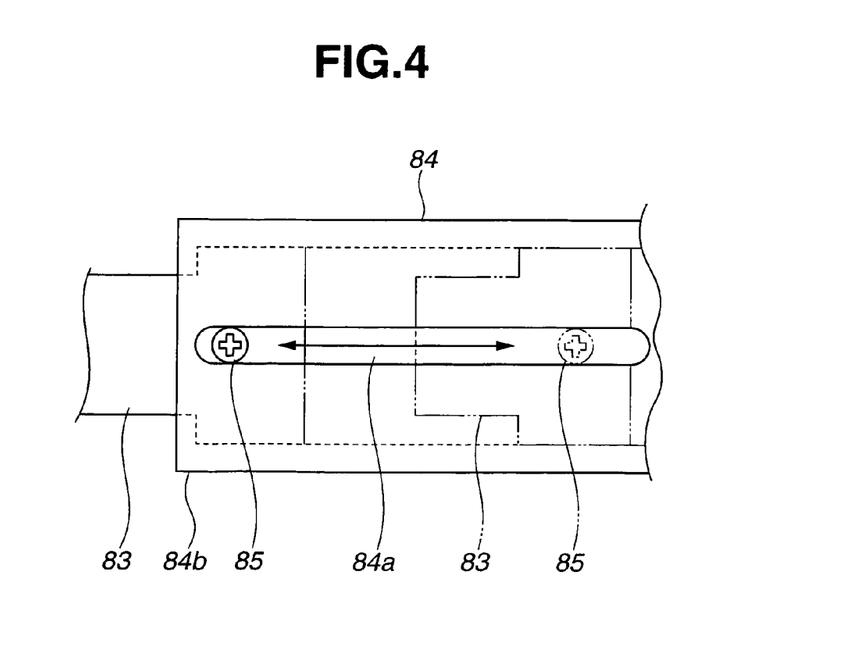
FIG. 4 is a plan view showing FIG. 3 seen from the direction of IV.
Figure 5:
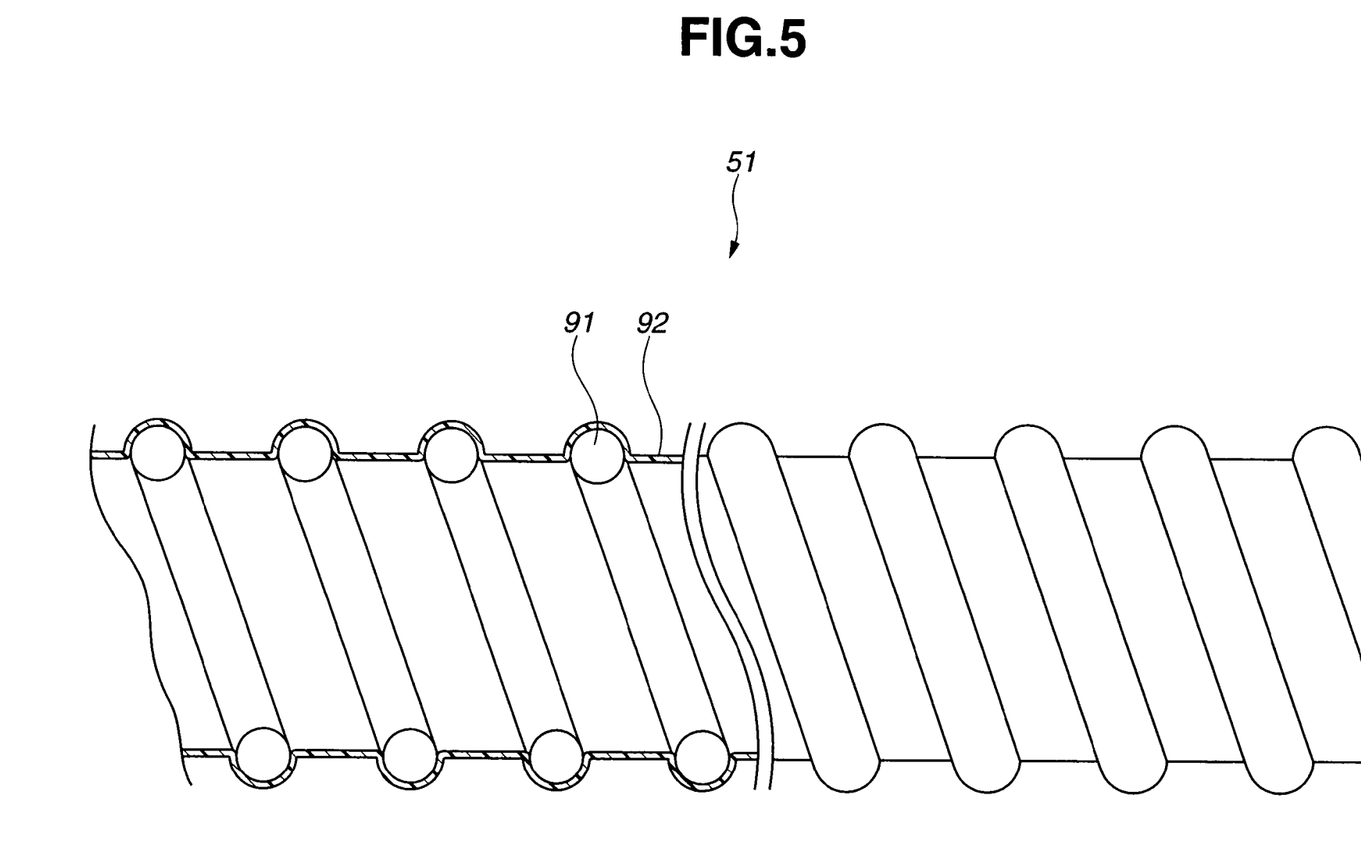
FIG. 5 is a plan view showing the spiral-shaped portion of FIG. 2.
Figure 6:
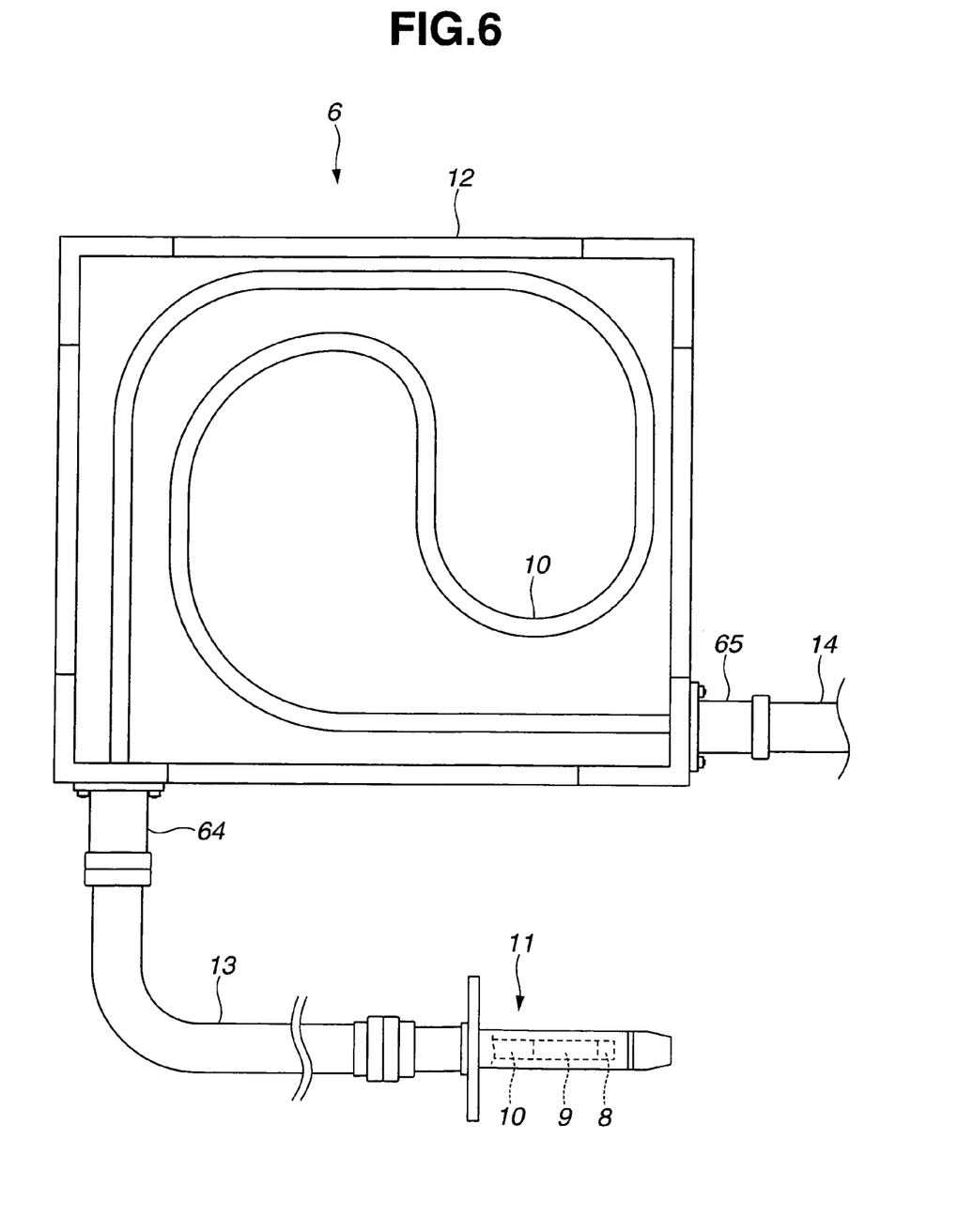
FIG. 6 is a top plan view showing a storage case of FIG. 1.
Figure 7:
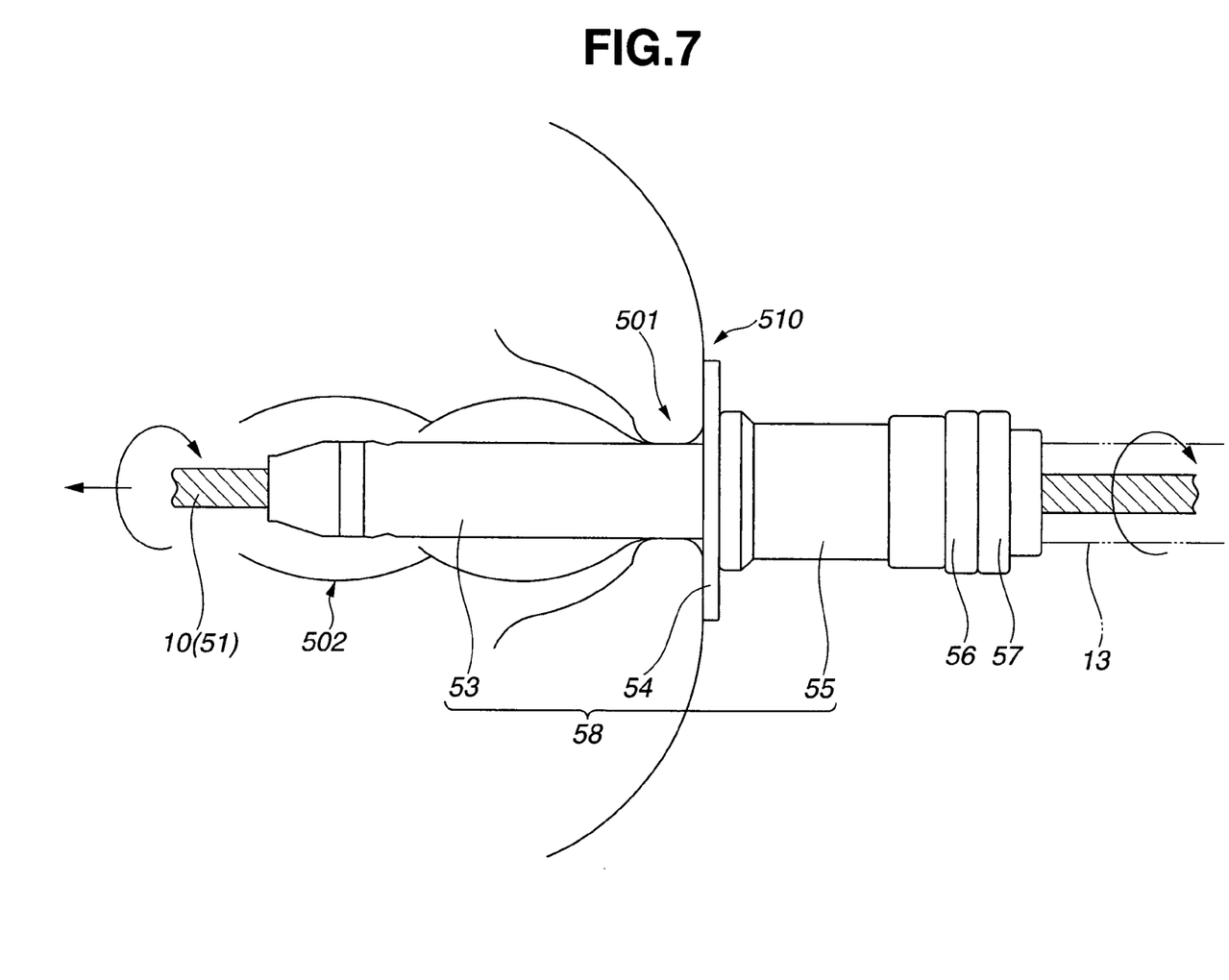
FIG. 7 is a plan view showing a state where an insertion-assisting instrument of FIG. 1 is inserted into a rectum from an anus of a patient.
Figure 8:
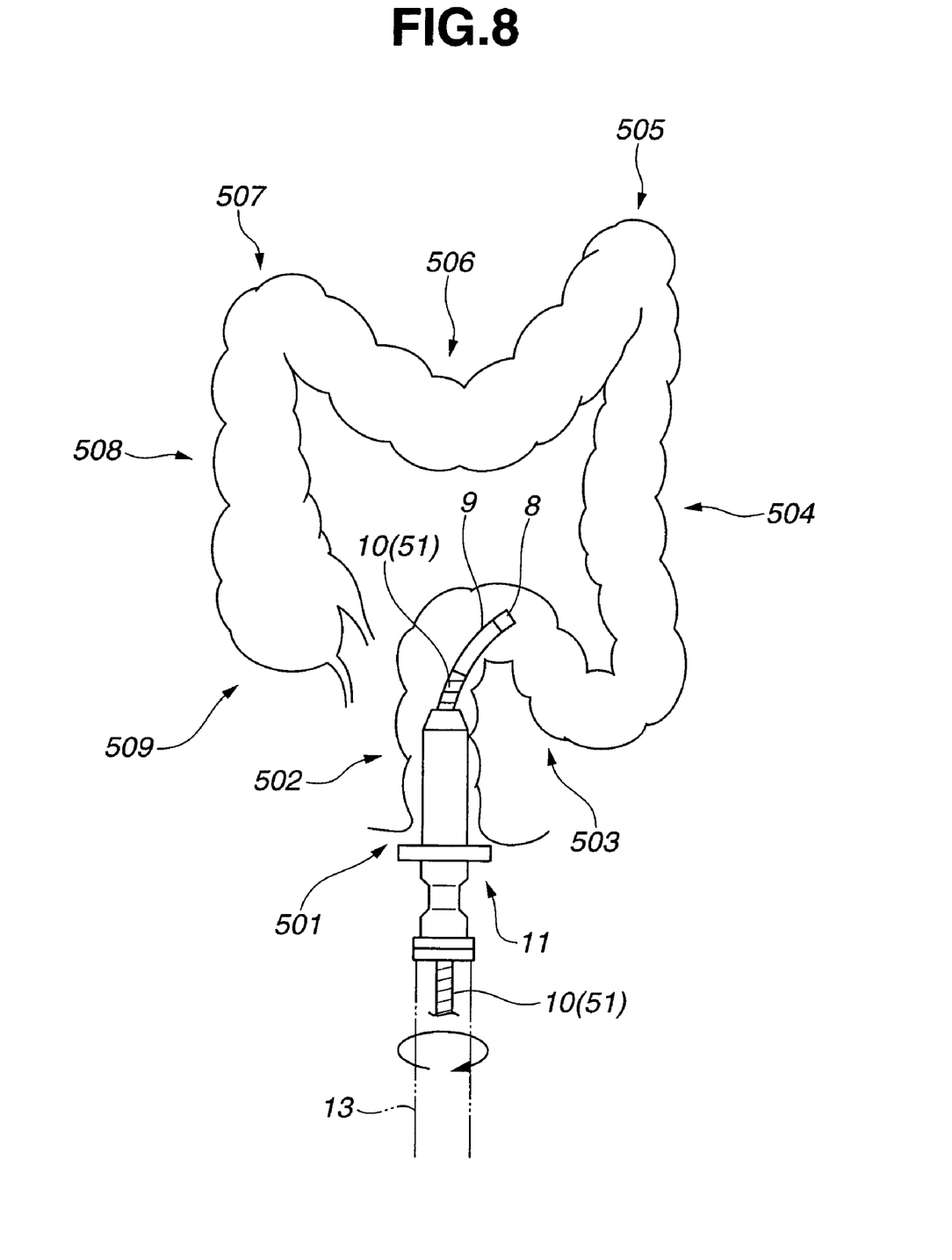
FIG. 8 is a plan view showing a state where an insertion portion main body of FIG. 1 inserted into a large intestine reaches a sigmoid colon.
Figure 9:
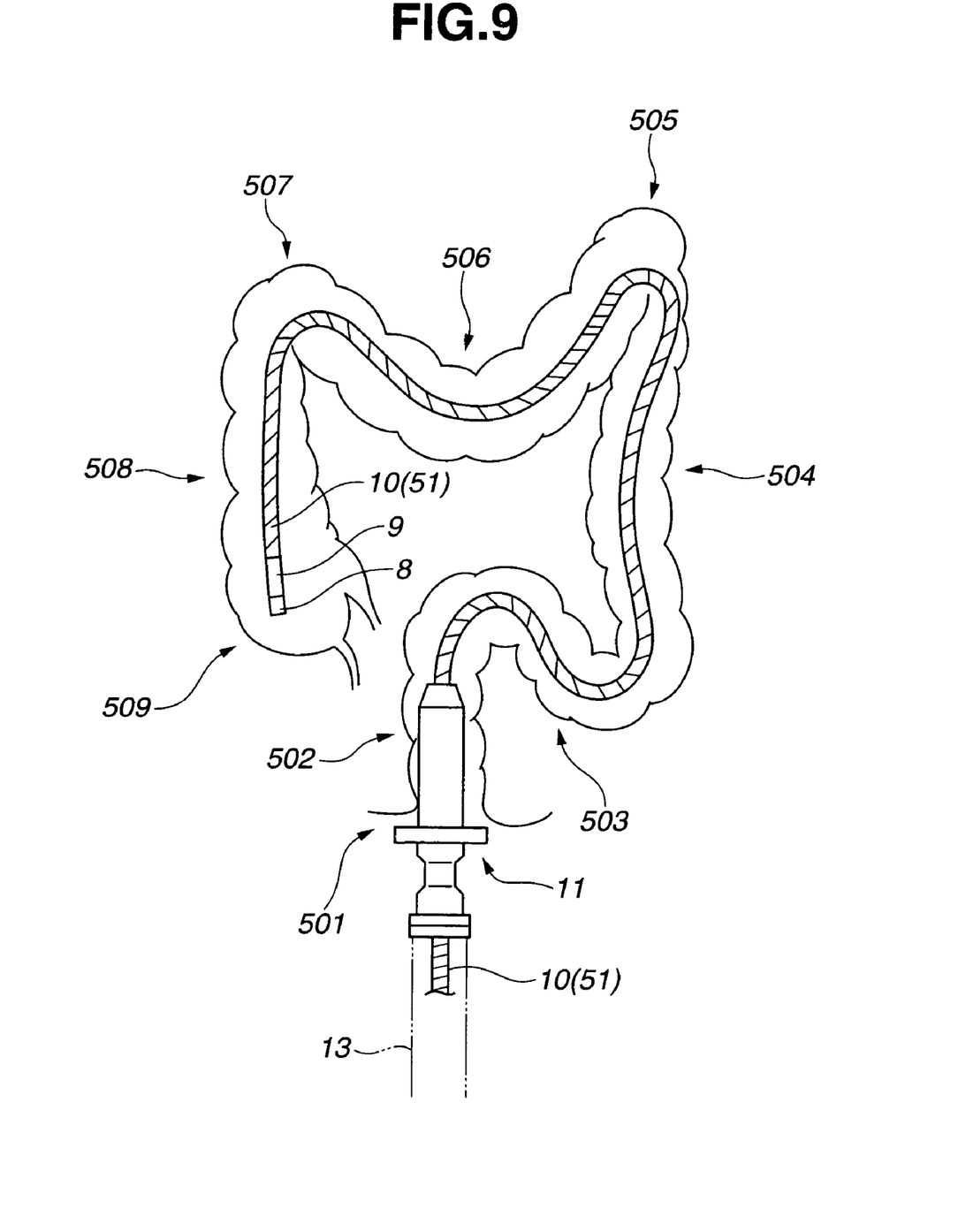
FIG. 9 is a plan view showing a state where the insertion portion main body of FIG. 8 inserted into the large intestine reaches a vicinity of a cecum.
Figure 10:
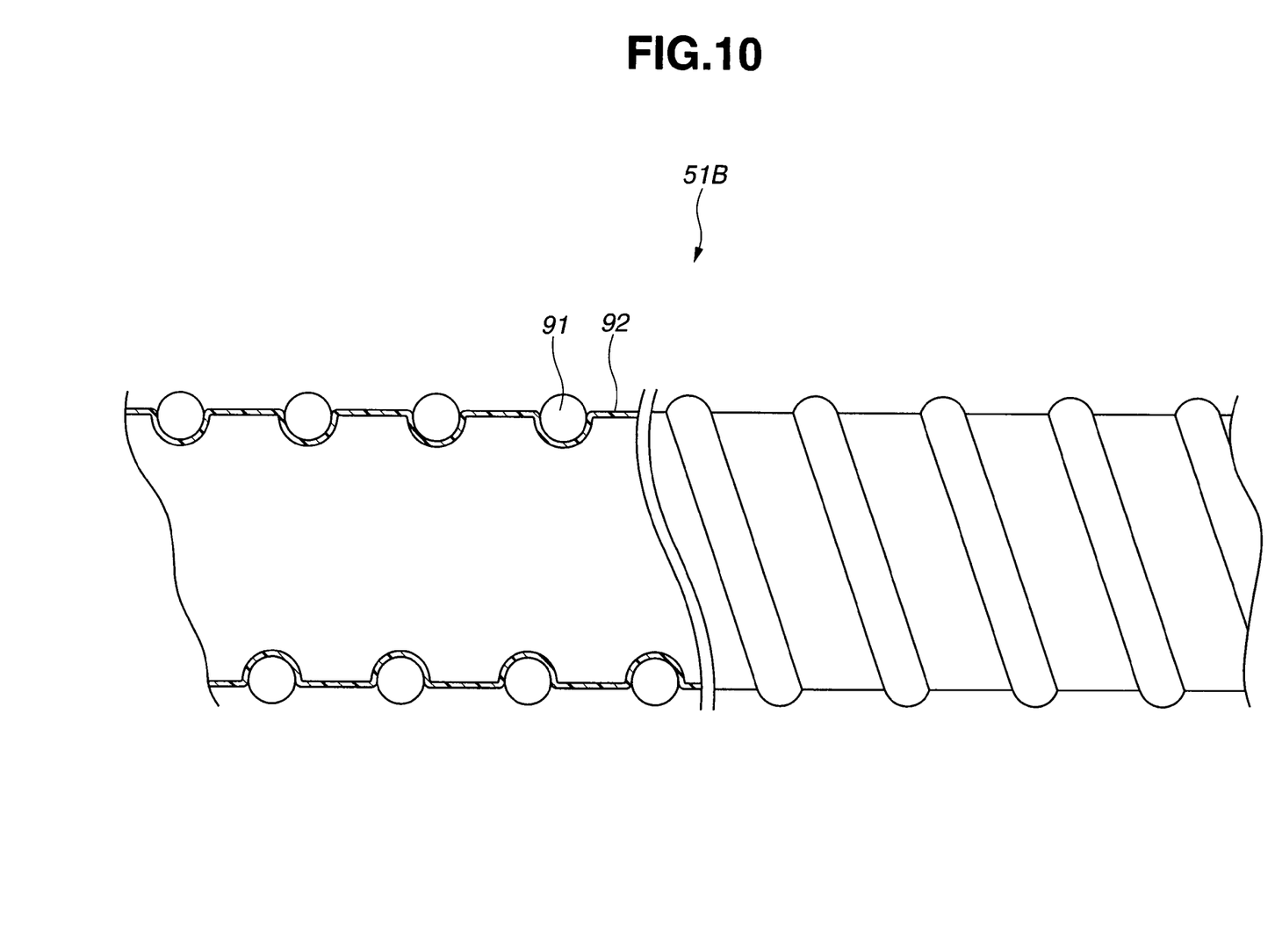
FIG. 10 is a plan view showing a modified example of the spiral-shaped portion of FIG. 5.

In addition, FIG. 3 is a cross-sectional view showing a part of a connector cover to which an operation portion-side guide tube of FIG. 1 is connected, FIG. 4 is a plan view showing FIG. 3 seen from the direction of IV, FIG. 5 is a plan view showing the spiral-shaped portion of FIG. 2, FIG. 6 is a top plan view showing a storage case of FIG. 1, FIG. 7 is a plan view showing a state where an insertion-assisting instrument of FIG. 1 is inserted into a rectum from an anus of a patient, FIG. 8 is a plan view showing a state where an insertion portion main body of FIG. 1 inserted into a large intestine reaches a sigmoid colon, FIG. 9 is a plan view showing a state where the insertion portion main body of FIG. 8 inserted into the large intestine reaches a vicinity of a cecum, and FIG. 10 is a plan view showing a modified example of the spiral-shaped portion of FIG. 5.

First, description will be made on a whole configuration of the rotating self-propelled endoscope system 1 with reference to FIG. 1.

As shown in FIG. 1, the rotating self-propelled endoscope system 1 includes a rotating self-propelled endoscope (hereinafter abbreviated simply as an endoscope) 2, a control device 3, a monitor 4, and a suction device 5.

The endoscope 2 includes an endoscope insertion portion (hereinafter abbreviated simply as an insertion portion) 6 and an operation portion 7. The insertion portion 6 includes, in the following order from a distal end thereof, a distal end rigid portion (hereinafter abbreviated simply as a distal end portion) 8, a bending portion 9, an insertion portion main body 10, an insertion-assisting instrument 11, an insertion portion storage case (hereinafter abbreviated simply as a storage case) 12, a distal end-side guide tube 13 which is a corrugated-shaped tube and is interposed between the insertion-assisting instrument 11 and the storage case 12, an operation portion-side guide tube 14 which is a corrugated-shaped tube and is interposed between the operation portion 7 and the storage case 12, and a connector cover 15 to which one end of the operation portion-side guide tube 14 is linked.

The operation portion 7 includes a motor box 16 as a rotation device, a grip portion 17, and a main operation portion 18. Note that the motor box 16 constitutes a part of the insertion portion 6.

The main operation portion 18 includes a bending operation knob 19 for bending the bending portion 9 of the insertion portion 6 in four directions, to be more precise, in up/down and left/right directions corresponding to an endoscope image acquired by the endoscope 2, buttons 20 for performing feeding or sucking operation of fluid, and switches 21 for performing various image-pickup operations and operating optical systems such as illumination, and the like.

The bending operation knob 19 includes generally disk-shaped two knobs rotatably provided so as to be coaxially superposed on one surface of the main operation portion 18 of the operation portion 7. These two knobs include an up/down bending operation knob 19a for operating the bending portion 9 in up/down directions of the endoscope image, and a right/left bending operation knob 19b for operating the bending portion 9 in right/left directions of the endoscope image.

The up/down bending operation knob 19a is disposed on a face side of the main operation portion 18. The right/left bending operation knob 19b is disposed coaxially with the up/down bending operation knob 19a so as to be located on outer side with respect to the face of the main operation portion 18 than the up/down operation knob 19a.

That is, the up/down bending operation knob 19a is disposed nearer to the main operation portion 18 than the right/left bending operation knob 19b. According to this, in the endoscope 2, the up/down bending operation of the up/down bending operation knob 19a which is often used in a normal endoscope operation can be easily performed.

The main operation portion 18 includes a universal cord 18a which is an electric cable extended from one side surface thereof. In addition, the main operation portion 18 includes a breaking prevention portion 18b provided at a root portion of the universal cord 18a from which it extends. On the extended end of the universal cord 18a, a connector portion 22 is provided. The connector portion 22 is connected to the control device 3.

In addition, the buttons 20 provided on another side surface of the main operation portion 18 include an air/water feeding button 20a to be operated in feeding air or feeding liquid into a subject from the distal end portion 8 of the endoscope 2, and a suction button 20b to be operated in sucking body fluid and the like in the subject from the distal end portion 8 of the endoscope 2.

From the connector cover 15, three tubes 23 inserted in the insertion portion 6 are extended. The three tubes 23 include an air feeding tube 23a, a water feeding tube 23b, and a suction tube 23c.

The extended ends of the three tubes 23 are connected to the control device 3 respectively at predetermined positions of a front surface portion of the control device via detachable connectors. To the control device 3, an air feeding tank 24 is detachably mounted. The air feeding tank 24 stores inside thereof distilled water or normal saline solution.

In the endoscope 2, when the air/water feeding button 20a of the main operation portion 18 is operated in a predetermined way, the distilled water or the normal saline solution is fed from the air feeding tank 24 to the water feeding tube 23b by operations of a compressor, a valve, and the like which are not shown, under the control of the control device 3, and the distilled water or the normal saline solution is spouted out from an channel opening formed at the distal end portion 8.

In addition, in the endoscope 2, when the air/water feeding button 20a of the main operation portion 18 is operated in a predetermined way, air is fed from the compressor to the air feeding tube 23a by the operations of the compressor, the valve, and the like which are not shown, under the control of the control device 3, and air is spouted out from the channel opening formed at the distal end portion 8.

Furthermore, in the endoscope 2, when the suction button 20b is operated, body fluid and the like in the subject is sucked from a suction channel opening of the distal end portion 8 similarly by the operations of the compressor, valve, and the like which are not shown, under the control of the control device 3. The sucked body fluid and the like are fed from the control device 3 via the suction tube 23c into the suction device 5 via a suction device tube 5a. Note that, though the suction device 5 is used in the rotating self-propelled endoscope system 1 according to the present embodiment, a suction system kept in a hospital may be used.

To the control device 3, a foot switch 25 for rotating the insertion portion main body 10 of the endoscope 2 in a predetermined direction or stopping the same is connected by an electric cable 25a. Note that, though not shown, a moving forward/backward switch for determining the rotation direction of the insertion portion main body 10 and stopping the insertion portion main body 10 is provided on the main operation portion 18 of the operation portion 7.

In addition, on the front surface portion of the endoscope 3, a power source switch, a dial for varying a rotation speed of the insertion portion main body 10 of the endoscope 2, and the like, are provided. Note that a motor not shown for applying a rotational force to the insertion portion main body 10 is built in the motor box 16 of the operation portion 7. Furthermore, the control device 3 is electrically connected with the monitor 4. On the monitor 4, an endoscope image acquired by the endoscope 2 is displayed.

Next, referring to FIG. 2, description will be made on the distal end portion 8, the bending portion 9, and the insertion portion main body 10, which constitute a part of the insertion portion 6 of the endoscope 2. First, the distal end portion 8 will be described.

The distal end portion 8 includes a main body annulus 26 formed in a generally circular ring shape by a resin having biocompatibility. Inside the main body annulus 26, an image-pickup unit 27 is provided. The image-pickup unit 27 has an outer shape formed by a holding annulus 28a of generally circular ring shape, a cover annulus 28b of generally circular ring shape, and a cover body 29 of dome shape.

The holding annulus 28a and the cover annulus 28b are formed by a metal having biocompatibility. The cover body 29 is formed by a transparent synthetic resin having biocompatibility. The holding annulus 28a is contained in the main body annulus 26. The cover annulus 28b is fitted to a proximal end side of the holding annulus 28a. The cover body 29 is fitted so as to airtightly seal a distal end opening portion of the holding annulus 28a.

Inside a space of the image-pickup unit 27, there are provided an objective lens group 30, an image-pickup element 31 such as an CCD (Charge Coupled Device) or CMOS (Complementary Metal Oxide Semiconductor) disposed at a light converging position of the objective lens group 30, and a flexible printed circuit board 32. To the flexible printed circuit board 32, an image signal photoelectrically converted by the image-pickup element 31 is inputted, and signal processing such as amplification is performed on the signal.

The flexible printed circuit board 32 has a signal cable 33 connected thereto. The signal cable 33 is inserted in the bending portion 9 and the insertion portion main body 10, to be connected to a connector not shown provided in the connector cover 15 (see FIG. 1).

An objective lens frame 30a for holding the objective lens group 30 is fixed to a holding body 35. The rear portion of the objective lens frame 30a fits into an image-pickup element frame 31a for holding the image-pickup element 31. On a back surface of the image-pickup element 31, a circuit board 31b is mounted. To the circuit board 31b, the flexible printed circuit board 32 is electrically connected.

In addition, the holding body 35 has a plurality of LEDs 34 as illumination portions provided so as to surround the objective lens group 30. Note that the holding body 35 is formed in a generally circular shape and fastened onto a proximal-side inner circumferential surface of the cover body 29 such that the objective lens group 30 is disposed generally on a central axis of the cover body 29. That is, the objective lens group 30 is disposed such that the optical axis thereof passes through generally on the central axis of the cover body 29.

The image-pickup unit 27 configured as such is disposed at a position eccentric with respect to a longitudinal central axis of the main body annulus 26, and is fixed to the main body annulus 26 by a distal end cap 36 provided in a distal end-side opening portion of the main body annulus 26.

In a gap formed between the holding annulus 28a of the image pickup unit 27 and the main body annulus 26, disposed are a distal end portion of the suction tube 23c and a suction tube 37, to a proximal end side of which the suction tube 23c is connected. A distal end portion of the suction tube 37 is fastened to the distal end cap 36.

The distal end cap 36 has a channel opening portion 38 formed thereon. Note that, though not shown, in the gap formed between the holding annulus 28a and the main body annulus 26, ducts communicating with the air feeding tube 23a and the water feeding tube 23b are similarly disposed, and channel opening portions of the ducts are also formed on the distal end cap 36.

Next, description will be made on the bending portion 9.

In the bending portion 9, a rigid distal-end bending piece 39 fitted to a proximal-end opening portion of the main body annulus 26 constituting the distal end portion 8, and a plurality of rigid bending pieces 40 are continuously provided so as to be rotatable by a pivotal support portion 40a.

The bending pieces 39, 40 are coated by a bending outer cover 41 formed by a flexible member such as a fluororubber having biocompatibility. A distal end portion of the bending outer cover 41 is fastened to the proximal end portion of the main body annulus 26 by a thread winding adhesion portion 42.

Into the plurality of bending pieces 40, four bending operation wires 44 (only two wires are shown in FIG. 2) inserted in the insertion portion main body 10 are extended. A wire guide 43 for holding a distal end side of each of the four bending operation wires 44 is projectedly formed on each of the inner circumferential surfaces of the plurality of bending pieces 40.

Each of the four bending operation wires 44 is inserted in the wire guide 43, and the distal end side thereof is held by the wire guide 43. Each of the four bending operation wires 44 includes a cylinder-shaped stopping members 45 soldered to the distal end thereof, and the respective stopping members 45 are engaged with stopping holes 39a formed on the distal-end bending piece 39.

The respective four stopping holes 39a are formed on a surface perpendicular to a longitudinal axis of the distal-end bending piece 39 at positions where the surface is divided into quarters such that the distances between the holes become generally equal. The rotation direction about the axis of the distal-end bending piece 39 is determined such that the stopping holes 39a are located corresponding to the up/down, right/left positions of the endoscope image, respectively. Therefore, the four bending operation wires 44 are held and fixed at four points separated from one another at an almost equal interval in up/down and right/left directions.

Furthermore, the other ends of the bending operation wire 44 are coated with coil pipes not shown, and inserted in the insertion portion main body 10 to be extended to the connector cover 15. Note that the bending operation wires 44 have wire stoppers not shown at the proximal end portions thereof. The wire stoppers of the respective bending operation wires 44, in a state where the connector cover 15 is integrated with the motor box 16, are linked so as to correspond respectively to wire connection members not shown provided in the grip portion 17.

The respective wire connection members are linked to a bending operation mechanism not shown and a chain not shown which work with the bending operation knob 19 provided in the main operation portion 18. That is, in the endoscope 2, when the bending operation knob 19 is operated and rotated, the respective wire connection members are alternately pulled or loosened by the bending operation mechanism, so that the respective bending operation wires 44 are pulled or loosened.

Therefore, in the endoscope 2, pulling or loosening the respective four bending operation wires 44 causes the distal-end bending piece 39 to face in any of up, down, right, and left directions, so that a plurality of bending pieces 40 follow the movement of the distal-end bending piece 39. As a result, the bending portion 9 is operated to be bent in any of up, down, right and left directions.

At the proximal end portion of the bending portion 9, provided are an inner layer tube base 47, formed by a metal, for fixing an inner layer tube which is fitted on an outer circumferential side of the bending piece 40 positioned proximalmost, and a spiral tube connection base 48, formed by a metal, for rotatably engaging a spiral-shaped portion 51 which is a rotating cylinder, described later, fitted on an outer circumferential side of the inner layer tube base 47. The bases are strongly fastened with adhesive and the like. Note that the bending outer cover 41 is fastened to the spiral tube connection base 48 by the thread winding adhesion portion 42. In addition, the spiral-shaped portion 51 is provided over the whole length of the insertion portion main body 10.

The inner layer tube base 47 has a proximal end portion to which a distal end portion of a flexible inner layer tube 49a inserted in the insertion portion main body 10 is fixed. The inner layer tube 49a may be a tube body having flexibility formed by knitting thin wires and the like in a cylindrical shape. Note that, inside of the inner layer tube 49a, inserted and provided are the bending operation wires 44, a signal cable 33, a power source cable for the LEDs 34, and the tubes 23 such as the air feeding tube 23a.

The spiral tube connection base 48 includes a projection 48a having a so-called snap-fit function at a proximal end portion thereof.

Next, the insertion portion main body 10 will be described.

The insertion portion main body 10 includes at the distal end thereof a distal end-side base 50 for linking-use which is formed by a synthetic resin and the spiral-shaped portion 51 of which distal end portion is fastened to the distal end-side base 50 with adhesive 52. The insertion portion main body 10 has the inner layer tube 49a provided inside thereof. That is, the inner layer tube 49a protects the respective components inside.

The distal end-side base 50 has at the distal end thereof an engaging portion 50a engaging with the projection 48a of the spiral tube connection base 48 to enable the snap-fit function. When the engaging portion 50a engages with the projection 48a of the spiral tube connection base 48, the distal end-side base 50 is connected to the spiral tube connection base 48 rotatably about the longitudinal axis thereof. The distal end-side base 50 is coated with the bending outer cover 41 such that a gap is formed on outer circumferential side thereof.

The spiral-shaped portion 51 integrally fastened to the distal end-side base 50 with the adhesive 52 is formed so as to be rotatable about the longitudinal axis in the insertion direction and to function as a propulsion force generating portion as described later. Note that a detailed configuration of the spiral-shaped portion 51 will be described later.

The spiral-shaped portion 51 is applied with a rotational force by a motor not shown provided in the motor box 16 (see FIG. 1) of the operation portion 7. When applied with the rotational force by the motor to be rotated, the spiral-shaped portion 51 contacts an inner wall of a body cavity of a subject to generate a propulsion force, and advances in the insertion direction thereof. At this time, the distal end-side base 50 fastened to the distal end portion of the spiral-shaped portion 51 comes into contact with the spiral tube connection base 48 to press the bending portion 9, so that a propulsion force is applied to allow the whole insertion portion main body 10 including distal end portion 8 to move forward to a deep portion in the body cavity.

Next, description will be made on a proximal end side of the spiral-shaped portion 51 with reference to FIGS. 3 and 4. First, a connection between the operation portion-side guide tube 14 and the connector cover 15 will be described.

The operation portion-side guide tube 14 is provided with a stop ring 81 for stopping the outer circumference of the proximal end portion thereof. The stop ring 81 is fitted and held at an inner circumference of a portion connected by screwing a fifth fixing annulus 78 formed by a generally cylindrical metal annulus with a connecting cylinder 79 formed by a synthetic resin. Note that the fifth fixing annulus 78 may be a rigid cylinder formed by the synthetic resin, plastic, and the like.

The fifth fixing annulus 78 is formed such that the middle portion thereof protrudes in an outer diameter direction, and has a male screw portion 78a formed on an outer circumference of the proximal portion thereof. In addition, the connecting cylinder 79 is formed such that the distal end portion thereof protrudes in the outer diameter direction, and has a female screw portion 79a formed on an inner circumferential surface of the distal end portion. Furthermore, the connecting cylinder 79 is extended in a multi-step form from the female screw portion 79a toward the proximal end side so that an outer circumferential diameter thereof becomes smaller, and has at a proximal end thereof a plurality of stopping portions 80 so as to be detachably attached to the connector cover 15.

That is, the fifth fixing annulus 78 and the connecting cylinder 79 are connected by screwing the male screw portion 78a in the female screw portion 79a, and in the connecting portion, the stop ring 81 is internally fitted and held.

In this state, the operation portion-side guide tube 14 is in a state where the proximal end portion thereof is compressed and the proximal outer circumferential portion thereof is pressed against an end surface with which the connecting cylinder 79 comes into contact. According to this, the operation portion-side guide tube 14 is connected to the fifth fixing annulus 78 and the connecting cylinder 79 kept in a watertight state.

The connecting cylinder 79 is connected with the connector cover 15 such that the stopping portion 80 is connected to the connector cover 15. In more detail, the connector cover 15 has a connecting portion 82 which is a cylinder including outward flanges 82a formed at a distal end and proximal end portions thereof. To the connecting portion 82, the connecting cylinder 79 is connected such that a plurality of stopping portions 80 of the connecting cylinder 79 is externally fitted.

The plurality of stopping portions 80 include at the proximal end thereof projections 80a projecting in the inner circumferential direction of the connecting cylinder 79. Therefore, the connecting cylinder 79 and the connector cover 15 are detachably connected with each other by hooking the projections 80a on the outward flanges 82a positioned on the proximal end portion of the connecting portion 82.

Furthermore, each of the projections 80a of the stopping portions 80 stops the outward flange 82a of the connecting cylinder 79, so that the connecting cylinder 79 is axially rotatable with respect to the connector cover 15. Accordingly, the operation portion-side guide tube 14 linking to the connecting cylinder 79 is also rotatably connected to the connector cover 15.

In such a connecting portion of the operation portion-side guide tube 14 and the connector cover 15, the proximal end portion of the spiral-shaped portion 51 is fastened to a proximal end-side base 83 with an adhesive 83a. The proximal end-side base 83 is fitted by insertion in a slide cylinder 84. In the slide cylinder 84, two slots 84a are symmetrically formed at upper and lower positions such that heads of male screws 85 are fitted in the slots.

In the proximal end-side base 83, female screw portions 83b are formed at positions corresponding to those of the slots 84a of the slide cylinder 84, and the male screws 85 are fitted in the female screw portions 83b. A proximal end side of the slide cylinder 84 is connected to a distal end portion of a rotational shaft 86 by fixing screws 87.

At a distal end side of the slide cylinder 84, a flange portion 84b is formed to prevent the proximal end-side base 83 from falling off. As shown in FIG. 4, the proximal end-side base 83 is slidable in a longitudinal direction between the flange portion 84b and the distal end side of the rotational shaft 86. According to this, even if torque is applied when rotating, the spiral-shaped portion 51 is extendable in the longitudinal direction and will not be rigid because of the sliding of the proximal end-side base 83, thereby preventing a decline in insertability. In addition, the rotational shaft 86 is rotatably supported in the connector cover 15, though not shown.

In the endoscope 2, when the connector cover 15 is connected with the motor box 16 (see FIG. 1), a gear not shown provided to the rotational shaft 86 and a gear not shown provided in the motor box 16 are meshed with each other. Then a driving force of the motor is conveyed to each gear, and through the rotational shaft 86 and the proximal end-side base 83, the spiral-shaped portion 51 rotates about the longitudinal axis. That is, the rotational force from the motor box 16 is conveyed to the spiral-shaped portion 51 from the proximal end portion. Note that the inner layer tube 49a inserted in the spiral-shaped portion 51 is so disposed as to be inserted through the rotational shaft 86 from inside of the connector cover 15 to reach the spiral-shaped portion 51.

Next, a detailed configuration of the spiral-shaped portion 51 will be described with reference to FIG. 5.

The spiral-shaped portion 51 is provided on the outer circumference of the inner layer tube 49a so as to be rotatable around the inner layer tube 49a as a central axis, and functions as the propulsion force generating portion. The spiral-shaped portion 51 is formed by a metal coil 91 having biocompatibility which is nondensely wound, and a resin thin film 92 having biocompatibility which is continuously provided so as to cover gaps of a wire forming the metal coil 91.

Wire diameter of the metal coil 91 is preferably set from not less than 0.6 millimeters to not more than 2.0 millimeters so as to obtain good followability to torque. In addition, an effective lead angle of the metal coil 91 is, for example, from 3 to 15 degrees so that a propulsion speed is suitable for an inspection. Note that the metal coil 91 is preferably a Ni (nickel)-free coil.

The resin thin film 92 is continuously provided to cover the gaps of the wire forming the metal coil 91 by coating the outer circumference of the metal coil 91 so as to fill in the gaps of the wire forming the metal coil 91. The resin thin film 92 is formed such that the resin hardness is from not less than 50 degrees to not more than 90 degrees and the thickness of the film is from not less than 0.03 millimeters to not more than 0.2 millimeters to obtain a good balance between flexibility and durability. A resin forming the resin thin film 92 is excellent in slidability, flexibility, and moldability, and the resin thin film is formed to be transparent, semitransparent, or dark color by the resin having biocompatibility, for example, urethane, thermoplastic resin, or polyester.

In this way, in the spiral-shaped portion 51, the resin thin film 92 is continuously provided to cover the gaps of the wire forming the metal coil 91 by coating the outer circumference of the metal coil 91 so as to fill in the gaps of the wire forming the metal coil 91. Therefore, peak portions of the spiral-shaped portion 51 can be formed to be high, so that the spiral-shaped portion is well caught by an inner wall of a body cavity. Accordingly, the propulsion force to be obtained becomes stronger. In addition, construction of the spiral-shaped portion 51 is easy due to high flexibility in design of the spiral angle and the like. Furthermore, the nondensely wound metal coil 91 is used, thereby reducing the weight of the spiral-shaped portion and improving operability of the insertion portion main body 10. Therefore, the spiral-shaped portion 51 can be constructed with reduced cost, and has high flexibility in design of the spiral angle and the like, while improving the operability of the insertion portion main body 10.

In addition, in the spiral-shaped portion 51, the resin thin film 92 does not protrude inwardly from the inner circumference of the metal coil 91, so that the spiral-shaped portion 51 is prevented from rotating together with the inner layer tube 49a and securely fixed to the proximal end-side base 83.

Furthermore, in the spiral-shaped portion 51, a clearance can be set so as not to compress the inner layer tube 49a (internal object), even if the resin thin film 92 as a coating protrudes inwardly when the metal coil 91 is bent maximally, so that the spiral-shaped portion 51 is prevented from rotating together with the inner layer tube 49a.

Also, the spiral-shaped portion 51 has extendablility. According to this, in a case where the distal end of the insertion portion hits an intestinal wall, or in other cases, the force of pressing the intestine by the distal end is slowly changed, thereby realizing an advantage of reducing a load on the intestine.

When manufacturing the spiral-shaped portion 51, the metal coil 91 is coated by winding a resin tape. At this time, the metal coil 91 is wound around a core member not shown at a predetermined pitch. The metal coil 91 wound around the core member is coated by the resin tape which is wound around the outer circumference such that parts as tabs for sticking overlap each other.

After coated with the resin tape, the spiral-shaped portion 51 is formed by heat-adhesion while being rotated in a continuous furnace. After the heat-adhesion, the core member is pulled out, and the spiral-shaped portion 51 is completed. Accordingly, in the spiral-shaped portion 51, the height of the peak portions is secured and thin film can be formed by winding the resin tape. Therefore, functionality is high, and uneven rotation during the heat-adhesion can be prevented, thereby enabling the resin thin film to be formed with an even thickness.

Note that, the spiral-shaped portion 51 may be formed so that shortly-formed metal coils 91 are joined by a pipe not shown. In this case, a long furnace is not required, thereby reducing equipment investment for the spiral-shaped portion 51 and the cost thereof.

Alternately, the spiral-shaped portion 51 may be heat-processed while being rotated, after molded by dipping. In this case, it is possible to obtain good productivity, and prevent the unevenness of resin thickness in the spiral-shaped portion 51.

Alternately, the spiral-shaped portion 51 may be formed by a corrugate method, that is, a continuous molding in which productivity is good, or by a continuous extrusion forming method in which productivity and functionality are good.

Note that, the spiral-shaped portion 51 may be configured such that the portion from the distal end to the middle is coated with the resin thin film 92, and the metal coil 91 is exposed at the proximal end side. In this case, a long furnace is not required, thereby reducing equipment investment for the spiral-shaped portion 51 and cost thereof.

Note that, in the spiral-shaped portion 51, a solid and liquid lubricant may be applied to inner circumferential surfaces of the metal coil 91 and the resin thin film 92 as a surface processing for improving lubricity. This prevents the spiral-shaped portion 51 from rotating together with the inner layer tube 49a. Alternately, a surface processing for improving lubricity may be applied on the outer circumferential surface of the spiral-shaped portion 51. This reduces rotational friction between the spiral-shaped portion 51 and the intestine, thereby reducing a load of a motor for driving the spiral-shaped portion.

In the rotating self-propelled endoscope system 1 according to the present embodiment configured in this way, the insertion portion 6 (see FIG. 1) includes the distal end portion 8, the bending portion 9, the insertion portion main body 10, and the portions from the insertion-assisting instrument 11 covering the above-described portions to the connector cover 15. The insertion portion 6 is configured to be disposable after each use. Note that, though the insertion portion 6 is disposable in the present embodiment, the insertion portion may be reusable, if sterilization and disinfection are performed sufficiently after use.

Next, an operation of the rotating self-propelled endoscope system 1 will be described. Note that, in the following description, description will be made with reference to FIGS. 6 to 9 with taking a large intestine endoscopy as an example.

First, the rotating self-propelled endoscope system 1 is prepared as described in FIG. 1. An operator inserts the insertion-assisting instrument 11 from an anus of a patient lying on a bed, for example. Note that the insertion portion main body 10 is contained in the storage case 12, forming a loop as shown in FIG. 6.

As shown in FIG. 7, in the insertion-assisting instrument 11, an abutting portion 54 abuts a buttocks 510 in the vicinity of an anus 501 of the patient, so that only an insertion tube 53 is inserted in a rectum 502 from the anus 501. That is, the abutting portion 54 prevents the whole of the insertion-assisting instrument 11 from being inserted in the rectum 502. At this time, the operator fixes the abutting portion 54 to the buttocks 510 with a tape, or the like.

In such a state, the operator grasps the grip portion 17 of the operation portion 7, and rotates the spiral-shaped portion 51 of the insertion portion main body 10 in the longitudinal direction by foot operation of the foot switch 25, or manual operation of the moving forward/backward switch provided to the main operation portion 18.

Note that, in a guide tube fixing member 64 of the storage case 12, a propulsion force is applied to the spiral-shaped portion 51 by utilizing a rotational force applied to the spiral-shaped portion 51 by fitting a rubber plate and the like to the spiral-shaped portion 51, though not shown.

The operator drives to rotate the motor provided in the motor box 16 of the operation portion 7 by the above-described foot or manual operation. The rotational force is transmitted to the spiral-shaped portion 51 from the proximal end portion to the distal end side, and thereby the whole of the spiral-shaped portion 51 axially rotates in a predetermined direction as shown by an arrow in FIG. 7 and is applied with a propulsion force from the guide tube fixing member 64 of the storage case 12.

The spiral-shaped portion 51 applied with the propulsion force presses the spiral tube connection base 48 by the distal end-side base 50 shown in FIG. 2. According to this, the whole of the insertion portion main body 10 including the distal end portion 8 and the bending portion 9 advances toward a deep part in the large intestine by the propulsion force of the spiral-shaped portion 51 through the distal end-side guide tube 13 and the insertion-assisting instrument 11.

The operator, instead of grasping to push forward the insertion portion main body 10, grasps lightly a holding pipe 55 of the insertion-assisting instrument 11 to advance the insertion portion main body 10 toward the deep part in the large intestine only by the propulsion force applied in the guide tube fixing member 64.

At this time, the contact state between the spiral-shaped portion 51 and folds of the intestinal wall is equal to a relationship between a male screw and a female screw. The spiral-shaped portion 51 smoothly moves forward by the propulsion force applied thereto in the guide tube fixing member 64 and a propulsion force generated by contacting the folds of the intestinal wall, and as a result, the insertion portion main body 10 moves from the rectum 502 to a sigmoid colon 503.

As shown in FIG. 8, the distal end portion 8 and the bending portion 9 included in the insertion portion main body 10 reach the sigmoid colon 503. At this time, the operator operates the bending operation knob 19 (see FIG. 1) of the main operation portion 18, while observing an endoscope image displayed on the monitor 4, and operates to bend the bending portion 9 in accordance with a curving state of the sigmoid colon 503.

The operator, by the bending operation of the bending portion 9, can make the distal end portion 8 smoothly pass through the sigmoid colon 503 to which the insertion operation is difficult, while making the distal end portion move forward by the insertion portion main body 10 to which propulsion force is applied.

As inserted into a deeper part of the large intestine, the insertion portion main body 10 becomes a state in which the propulsion force is constantly applied thereto in the guide tube fixing member 64, and contacting length of the spiral-shaped portion 51 and the intestinal wall becomes longer.

Therefore, the insertion portion main body 10 can obtain a stable propulsion force in the direction of the deep part of the large intestine, even in a state where a part of the spiral-shaped portion 51 contacts folds of the sigmoid colon 503, a state where the insertion portion main body 10 is curved in a complex form, or the like.

In addition, having sufficient flexibility, the insertion portion main body 10 smoothly moves forward along the intestinal wall without changing the way the sigmoid colon 503, of which position easily changes, runs.

Furthermore, as described above, as for the spiral-shaped portion 51, the resin thin film 92 is continuously provided to cover the gaps of the wire forming the metal coil 91 by coating the outer circumference of the metal coil 91 so as to fill in the gaps of the wire forming the metal coil 91. Therefore, for example, compared with a configuration in which a densely wound coil is used, the weight of the spiral-shaped portion is remarkably reduced and propulsion of the insertion portion main body 10 is greatly improved.

In addition, since the weight of the whole of the insertion portion 6 is reduced, there is an advantage that labor in transporting and setting the insertion portion is reduced. Furthermore, the spiral-shaped portion 51 has high flexibility in design of the spiral angle, so that it is easy to increase the propulsion force generated by the contact with the intestinal wall by increasing the spiral angle.

The insertion portion main body 10 passes through the sigmoid colon 503, and then a curved portion which is a boundary between the sigmoid colon 503 and a descending colon 504 of low mobility, and a splenic flexure 506 which is a boundary between the descending colon 504 and a transverse colon 505 of high mobility, and then smoothly advances along the wall of hepatic flexure 507 which is a boundary between the transverse colon 505 and an ascending colon 508, to reach, for example, in the vicinity of a cecum 509 which is a target site without changing the way the large intestine runs, as shown in FIG. 9.

In this insertion operation, when the distal end portion 8 reaches the splenic flexure 506 and the hepatic flexure 507, the operator, same as described above, operates the bending operation knob 19 of the main operation portion 18 while observing an endoscope image displayed on the monitor 4, to perform bending operation in accordance with the curving state of each site.

After determining that the distal end portion 8 has reached in the vicinity of the cecum 509 based on the endoscope image on the monitor 4, the operator once stops the rotation of the spiral-shaped portion 51 by the above-described foot or manual operation. The operator performs an operation for rotating the spiral-shaped portion 51 in a direction opposite to the axial rotation direction at the time of insertion, by the foot operation of the foot switch 25 or the manual operation of the moving forward/backward switch provided to the main operation portion 18.

That is, the operator performs an inspection of the large intestine while rotating the spiral-shaped portion 51 in the direction opposite to the rotation direction at the time of insertion, and moving the insertion portion main body 10 backward in a direction in which the distal end portion 8 is withdrawn from the deep part of the large intestine, that is, in the vicinity of the cecum 509.

The operator can move the insertion portion main body 10 backward by a retreat force applied to the spiral-shaped portion 51 in the guide tube fixing member 64, without touching the insertion portion main body 10. In addition, the whole of the insertion portion main body 10 moves backward by the propulsion force of the spiral-shaped portion 51, since the distal end portion 8 and the bending portion 9 are pulled by the spiral-shaped portion 51 by the snap-fit function.

When the distal end portion 8 of the insertion portion main body 10 has reached the insertion-assisting instrument 11, the operator withdraws the insertion portion main body 10 together with the insertion-assisting instrument 11 from the anus 501 of the patient and terminates the inspection in the large intestine. At this time, the insertion portion main body 10 is applied with the retreat force in the guide tube fixing member 64, and stored in the storage case 12 while being bent so as to return to the original state as shown in FIG. 6.

As described above, the rotating self-propelled endoscope system 1 according to the present embodiment has a configuration with excellent insertability in which the insertion portion main body 10 can be easily inserted into the deep part of the large intestine.

Furthermore, the endoscope 2 according to the present embodiment includes the guide tubes 13, 14 having flexibility, which link the storage case 12 with the insertion-assisting instrument 11 or the operation portion 7 so as to communicate with each other.

Therefore, the endoscope 2 according to the present embodiment can be moved to a desired position within a predetermined allowable range, since the grip position of the operation portion 7 by the operator and the position of the insertion-assisting instrument 11 approaching to an anus of a patient are not limited, even if the storage case 12 is placed and fixed.

That is, in the endoscope 2 according to the present embodiment, the distal end-side guide tube 13 connecting the insertion-assisting instrument 11 and the storage case 12 is a flexible tube, so that the positional relationship between the anus of the patient and the storage case 12 is not required to be constant.

In addition, in the endoscope 2 according to the present embodiment, also the operation portion 7 is not limited in movement thereof due to the flexibility of the operation portion-side guide tube 14.

Furthermore, the operator can visually confirm the movement of the insertion portion main body 10, in particular, the rotating state of the spiral-shaped portion 51, because the storage case 12, and the guide tubes 13, 14 are formed by a transparent or semi-transparent material.

Moreover, in the endoscope 2 according to the present embodiment, from the insertion-assisting instrument 11, the distal end-side guide tube 13, the storage case 12, to the operation portion-side guide tube 14, the respective connecting portions are formed to be watertight. Therefore, the endoscope 2 prevents liquid such as filth in the large intestine from being scattered in a treatment room. As a result, the insertion portion 6 has a hygienically excellent configuration.

In addition, the insertion portion main body 10 does not receive resistance such as constriction by the anus 501 of the patient before insertion into the body cavity, due to the insertion-assisting instrument 11, thereby reducing generation of deflection and preventing twisting by rotation.

Furthermore, the insertion portion main body 10 does not directly contact the anus 501 when inserted into the large intestine, due to the insertion-assisting instrument 11. Therefore, the insertion portion main body 10 having high flexibility has improved insertability into the large intestine, because the insertion portion main body 10 does not receive the resistance such as the constriction by the anus 501.

As a result, the endoscope 2 and the insertion portion 6 thereof have a configuration with great operability, because the insertion portion main body 10 and the spiral-shaped portion 51 can be smoothly inserted into a subject site.

In addition, in the spiral-shaped portion 51 of the present embodiment, the resin thin film 92 is continuously provided to cover the gaps of the wire forming the metal coil 91 by coating the outer circumference of the metal coil 91 so as to fill in the gaps of the wire of the nondensely wound metal coil 91, so that the spiral-shaped portion 51 has a flexibility in design of the spiral angle and the like with reduced cost, and is excellent in the force for propelling the insertion portion and in handling such as transportation, setting, and the like due to the reduced weight.

Note that, in the above-described spiral-shaped portion 51, the resin thin film is continuously provided to cover the gaps of the wire forming the metal coil 91 by coating the outer circumference of the metal coil 91 so as to fill in the gaps of the wire forming the metal coil 91. However, the spiral-shaped portion may be formed as shown in FIG. 10.

As shown in FIG. 10, in the spiral-shaped portion 51B, the resin thin film is continuously provided to cover the gaps of the wire forming the metal coil 91 by coating the inner circumference of the metal coil 91 so as to fill in the gaps of the wire forming the metal coil 91. According to this, the spiral-shaped portion 51B has an improved slip property in the rotation direction compared with the spiral-shaped portion 51 according to the present embodiment, thereby reducing a load of motor applying a rotational driving force.

Note that, though the rotational driving force of the motor built in the motor box 16 is transmitted to the proximal end side of the spiral-shaped portion 51 which is a rotating cylinder to move and rotate the whole of the spiral-shaped portion 51 in the present embodiment, the configuration is not limited to the same. For example, it may be configured such that the rotational driving force of the motor is transmitted to the middle portion or the distal end portion of the spiral-shaped portion 51 to move and rotate the whole of the spiral-shaped portion 51.

It is to be understood that the invention described in the above embodiment is not limited to the same, and various modification may be implemented without departing from the scope of the invention. The aforementioned embodiments contain the invention in various stages such that a plurality of disclosed components may be arbitrarily combined for the purpose of providing various types of the invention.

For instance, even if some of the configuration requirements are deleted out of all the configuration requirements indicated in the embodiments, the configuration having the configuration requirements deleted therefrom can be extracted as an invention in the case where the problems described in the means for solving the problem can be solved and the effects described in advantages of the invention can be obtained.

Having described the preferred embodiments of the invention referring to the accompanying drawings, it should be understood that the present invention is not limited to those precise embodiments and various changes and modifications thereof could be made by one skilled in the art without departing from the spirit or scope of the invention as defined in the appended claims.

What is claimed is:

1. An endoscope for applying a propulsion force in a direction of insertion axis of an insertion portion in accordance with rotation of the insertion portion around the insertion axis based on a driving force of a driving member, the endoscope comprising:
   a flexible elongated inner layer tube in which bending operation wires for bending a bending portion provided in the insertion portion, a signal cable of an image-pickup unit provided in the insertion portion, a power source cable for a light source provided in the insertion portion, and tubes for air feeding, water feeding and suction provided at the insertion portion are inserted, and which protects the wires, the cable and the tubes for air feeding, water feeding and suction configured as a shaft of the insertion portion;
   a spiral-shaped portion rotatable around the inner layer tube as an axial center based on the driving force of the driving member, the spiral-shaped portion forming an outer surface of the insertion portion, and covering an outer circumference of the inner layer tube such that a clearance is formed between the spiral-shaped portion and the inner layer tube; and
   a connection element having a first portion disposed on the flexible elongated inner layer tube and a second portion disposed on the spiral-shaped portion, the second portion being rotatably engaged with the first portion;
   wherein, the spiral-shaped portion includes a nondensely wound metal coil and a resin thin film continuously provided so as to cover gaps of a wire forming the metal coil.

2. The endoscope according to claim 1, wherein either an outer circumference or an inner circumference of the spiral-shaped portion is coated with the resin thin film.

3. The endoscope according to claim 2, wherein at least a front half part of the metal coil in the direction of insertion axis of the insertion portion is coated with the resin thin film.

4. The endoscope according to claim 2, wherein a surface treatment agent for improving lublicity is applied to the inner circumference of the metal coil and an inner circumference of the resin thin film.

5. The endoscope according to claim 2, wherein a surface treatment agent for improving lublicity is applied to an outer circumference of the resin thin film.

6. The endoscope according to claim 1, wherein the metal coil and the resin thin film is extendable in the direction of insertion axis of the insertion portion.

7. The endoscope according to claim 1, wherein the wire is formed to have a diameter of from not less than 0.6 millimeters to not more than 2.0 millimeters.

8. The endoscope according to claim 1, wherein the wire is wound at a lead angle of not less than 3 degrees to not more than 15 degrees.

9. The endoscope according to claim 1, wherein the resin thin film has a hardness of not less than 50 degrees to not more than 90 degrees and formed to have a thickness of not less than 0.03 millimeters to not more than 0.20 millimeters.

10. An endoscope system comprising:
    the endoscope according to claim 1; and
    the driving member for moving and rotating the spiral-shaped portion of the endoscope about the insertion axis of the insertion portion such that the inner layer tube becomes an axial center.

11. An endoscope system comprising:
    the endoscope according to claim 2; and
    the driving member for moving and rotating the spiral-shaped portion of the endoscope about the insertion axis of the insertion portion such that the inner layer tube becomes an axial center.

12. The endoscope according to claim 1, wherein there is formed a clearance between the spiral-shape portion and the inner layer tube such that the inner layer tube is not pressed even if the resin thin film protrudes inwardly when the metal coil is bent maximally.

* * * * *